(12) United States Patent
Bester (10) Patent No.: US 6,210,415 B1
(45) Date of Patent: Apr. 3, 2001

(54) SURGICAL DRILL GUIDE

(75) Inventor: Leon W. Bester, Belmont, MA (US)

(73) Assignee: Lab Engineering & Manufacturing, Inc., North Billerica, MA (US)

( * ) Notice: Subject to any disclaimer, the term of this patent is extended or adjusted under 35 U.S.C. 154(b) by 0 days.

(21) Appl. No.: 09/507,771

(22) Filed: Feb. 18, 2000

(51) Int. Cl.[7] ................................................ A61B 17/90
(52) U.S. Cl. ............................................................. 606/96
(58) Field of Search .................................. 606/96, 86

(56) References Cited

U.S. PATENT DOCUMENTS

| | | | |
|---|---|---|---|
| 4,614,187 | 9/1986 | Mulhollan et al. | 128/303 |
| 4,739,751 | 4/1988 | Sapega et al. | 128/92 |
| 4,920,958 | 5/1990 | Walt et al. | 128/92 |
| 5,154,720 | 10/1992 | Trott et al. | 606/96 |
| 5,163,940 | 11/1992 | Bourque | 606/96 |
| 5,269,786 | 12/1993 | Morgan | 606/96 |
| 5,327,896 | 7/1994 | Schmieding | 128/753 |
| 5,350,383 | 9/1994 | Schmieding et al. | 606/96 |
| 5,409,493 | 4/1995 | Greenberg | 606/96 |
| 5,409,494 | 4/1995 | Morgan | 606/96 |
| 5,458,602 | 10/1995 | Goble et al. | 606/96 |
| 5,466,243 | 11/1995 | Schmieding et al. | 606/232 |
| 5,562,664 | 10/1996 | Durlacher et al. | 606/96 |
| 5,575,801 | 11/1996 | Habermeyer et al. | 606/148 |
| 5,613,971 | 3/1997 | Lower et al. | |
| 5,851,207 | * 12/1998 | Cesarone | 606/96 X |

* cited by examiner

*Primary Examiner*—Jeffrey A. Smith
(74) *Attorney, Agent, or Firm*—George A. Herbster; Pearson & Pearson (57) ABSTRACT

A surgical drill guide for directing a guide tube toward a target. The guide tube has first and second sets of teeth extending along an exterior surface thereof. A through passage in an operating mechanism housing receives the guide tube. A first actuator or guide tube advancing mechanism uses a ratchet and pawl mechanism to advance the guide tube distally. A guide tube locking mechanism, that includes another ratchet and pawl mechanism prevents any unwanted proximal motion by providing a releasable lock against any unwanted proximal motion of the guide tube during use.

20 Claims, 7 Drawing Sheets

SURGICAL DRILL GUIDE

BACKGROUND OF THE INVENTION

1. Field of the Invention

This invention generally relates to surgical drill guides and more specifically to an improved surgical drill guide that provides positive position control of a drill guide tube, particularly during arthroscopic surgical procedures.

2. Description of Related Art

Surgical drill guides are well known in the art. They are very useful in enabling a surgeon to locate a drill guide tube with accuracy relative to adjacent anatomical structures. Generally these drill guides include a housing with a passage for a guide tube that extends along a guide tube axis. A handle portion of the surgical drill guide carries both the housing and a probe with a target end. The probe positions the target end at a location on a bone that intersects the guide tube axis. Generally some mechanism associated with the housing enables the guide tube to move along the axis into contact with the bone so the bone lies on a line between the distal end of the guide tube and the target. Once positioned, a guide is advanced through the guide tube and driven into the bone. Then the guide tube is removed from the guide and the surgical drill guide is removed from the patient. The guidewire enables the surgeon to position a drill bit at the bone and perform any necessary drilling operation.

It is important that the guide tube remain fixed against the bone while the guidewire is being inserted. That is, once the guide tube is in position, some mechanism must prevent inadvertent proximal displacement of the guide tube. However, that mechanism must readily allow the guide tube to be removed once the guidewire is affixed to the bone. The following patents disclose number of examples of such mechanisms:

U.S. Pat. No. 4,920,958 (1990) Walt et al.
U.S. Pat. No. 5,154,712 (1992) Trott et al.
U.S. Pat. No. 5,163,940 (1992) Bourque
U.S. Pat. No. 5,458,602 (1995) Goble et al.
U.S. Pat. No. 5,613,971 (1997) Lower et al.

U.S. Pat. No. 4,920,958 discloses one embodiment of a drill guide assembly with a cannular elongated wire guide for directing a guide wire. The wire guide can slide longitudinally along its axis. A locking spring prevents movement of the wire guide proximally after it is positioned. The locking spring produces sufficient sliding friction between the spring and the wire guide to prevent inadvertent wire guide motion. With this system a surgeon uses two hands to move the wire guide without interference from the locking spring or uses sufficient force to overcome the sliding friction that produces the original locking action.

U.S. Pat. No. 5,154,720 discloses a drill guide in which a cylindrical guide tube is secured to a handle so that it may not be easily longitudinally moved in either direction without the user engaging a thumb activated locking mechanism. The cylindrical guide tube passes through a conically tapered cylindrical bore within the drill guide. A similarly tapered split collet is interposed concentrically between the exterior of the cylindrical guide tube and the interior of the bore. This collet has a plurality of longitudinally extending lobes which are sufficiently resilient so that movement of the collet to its proximal-most position causes the lobes to squeeze inwardly against the cylindrical guide tube. Friction engagement between the collet lobes and the guide tube prevents the guide tube from moving until the collet is moved distally to release pressure on the lobes. The collet is normally biased proximally by a leaf spring attached to the drill guide handle. A thumb activated lever moves the leaf spring distally to release pressure on the lobes and unlock the cylindrical guide tube.

The locking function disclosed in U.S. Pat. No. 5,154,720 seems entirely dependent upon the capability of the mechanism to exert sufficient sliding friction to prevent unwanted motion of the guide tube. In addition, it appears that a surgeon must use two hands to move the wire guide without interference or must apply a sufficient force to the guide tube to overcome the sliding friction that produces the original locking action.

U.S. Pat. No. 5,163,940 discloses a surgical drill guide for tibia. This surgical drill guide includes an arcuate support beam having a drill guide locator and locator probe. The drill guide locator holds a cannulated drill sleeve or tube by means of a sleeve locking mechanism. The sleeve locking mechanism comprises a cam surface trigger lock with an inclined surface and biased plunger member. When the sleeve locking mechanism is operated, a latch housing manually moves between a locked position and an unlocked position. In a locked position the cam surface engages a plunger pin and in turn forces the pin housing against the guide sleeve or tube. The surgical drill guide also includes a plunger that prevents the sleeve from being dislodged or falling out when the device is moved or utilized while the locking mechanism is unlocked. In this reference locking the guide tube also relies upon sliding friction. Moreover, a surgeon must manipulate the guide tube directly to advance the guide tube to a final position.

U.S. Pat. No. 5,458,602 also discloses a surgical drill guide with a mechanism for advancing the guide tube and locking the guide tube in place. The advancing mechanism comprises a single-fold leaf spring and gripper plate through which the guide tube passes. A surgeon can index the guide tube or sleeve into position by depressing a trigger as by moving a thumb off a locking lever and onto an adjacent trigger. Depressing the trigger causes its cam portion to engage the gripper plate so that it engages the outer surface of the guide tube and advances the tube distally. Upon releasing pressure from the trigger, the leaf spring urges the gripper plate proximally and locks the guide sleeve in place. To remove the drill sleeve, a surgeon engages a lock release gripper to compress the leaf spring and release the edge of the plate from the drill sleeve.

U.S. Pat. No. 5,613,971 discloses another surgical drill guide in which the guide sleeve includes teeth along a portion of its circumference. In an operating position, the teeth face a double-toothed pawl. As a surgeon pushes the guide tube distally, the guide tube passes the pawl that is spring loaded so that upon release of the guide tube the pawl locks against a tooth and prevents any proximal displacement of the tube. The surgeon unlocks the guide tube by twisting the guide tube so that the teeth are angularly displaced from the pawl whereupon the guide tube can be removed as the pawl slides over a smooth surface on the guide tube.

With the exception of U.S. Pat. No. 5,613,971, the foregoing prior art generally discloses mechanisms for preventing inadvertent proximal motion of a guide tube that depend upon sliding friction forces to lock the guide tube. With the exception of U.S. Pat. No. 5,458,602 each of the surgical drill guides in the aforementioned prior art requires a surgeon to manipulate the guide tube directly in order to advance the guide tube to a final position against a bone. While the use of a pawl for engaging teeth on a guide tube is disclosed in U.S. Pat. No. 5,613,971, that specific embodiment merely requires a surgeon to rotate the guide tube to defeat the lock. It appears possible to produce such a rotation inadvertently so that the ability of the mechanism to hold the guide tube against the bone becomes unreliable.

SUMMARY

Therefore it is an object of this invention to provide a surgical drill guide that provides positive positioning of the guide tube during use.

Another object of this invention is to provide a surgical drill guide in which a guide tube is positioned using positive interference between two elements rather than sliding friction.

Still another object of this invention is to provide a surgical drill guide that provides separate controls for advancing a guide tube toward a bone and locking the guide tube in position after it contacts the bone.

Yet another object of this invention is to provide a surgical drill guide that provides separate controls for advancing a guide tube toward a bone and locking the guide tube in position after it contacts the bone that is relatively easy for a surgeon to use.

Still another object of this invention is to provide a surgical drill guide that provides separate controls for advancing a guide tube toward a bone and locking the guide tube in position after it contacts the bone and that facilitates manufacture.

In accordance with this invention, a surgical drill guide comprises a body having a base portion with a cylindrical passage extending therethrough along an axis, a handle extending obliquely from the base portion and an arm extending obliquely to a free end positioned on the axis. A guide tube is adapted for being moved longitudinally through the cylindrical passage of the body. The guide tube has a first and second sets of ratchet teeth formed on angularly displaced faces of the guide tube. A handle pivoted from the body engages the first set of ratchet teeth for advancing the guide tube along the axis toward the free end of the arm. A lever pivoted in the body is biased to a first position. In this position the lever engages the second set of ratchet teeth for preventing any distal motion of the guide tube. In a second position the lever disengages from the second set of ratchet teeth thereby to enable distal movement of the guide tube away from the arm.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
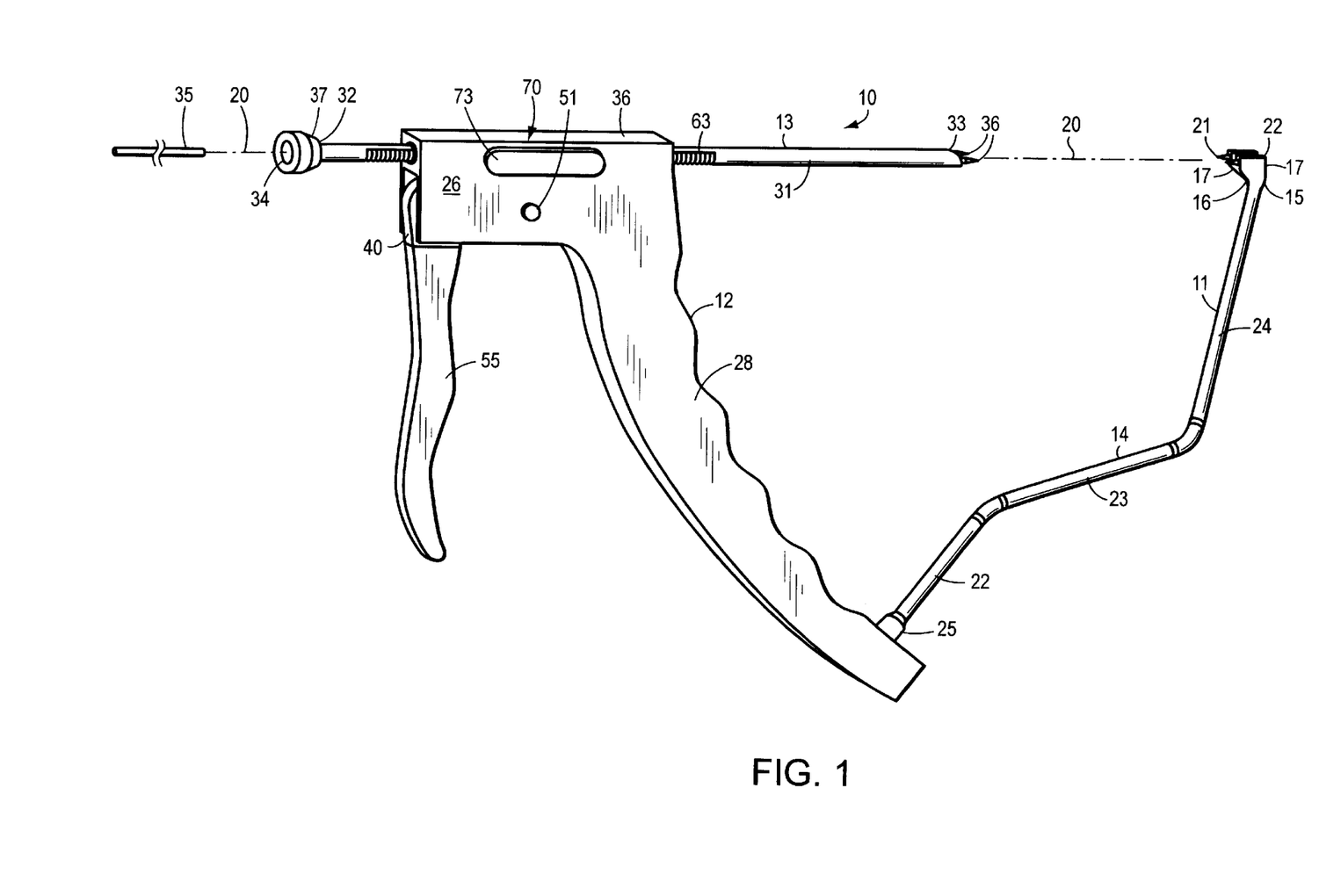
FIG. 1 is a perspective view of a surgical drill guide constructed in accordance with this invention.
Figure 2:
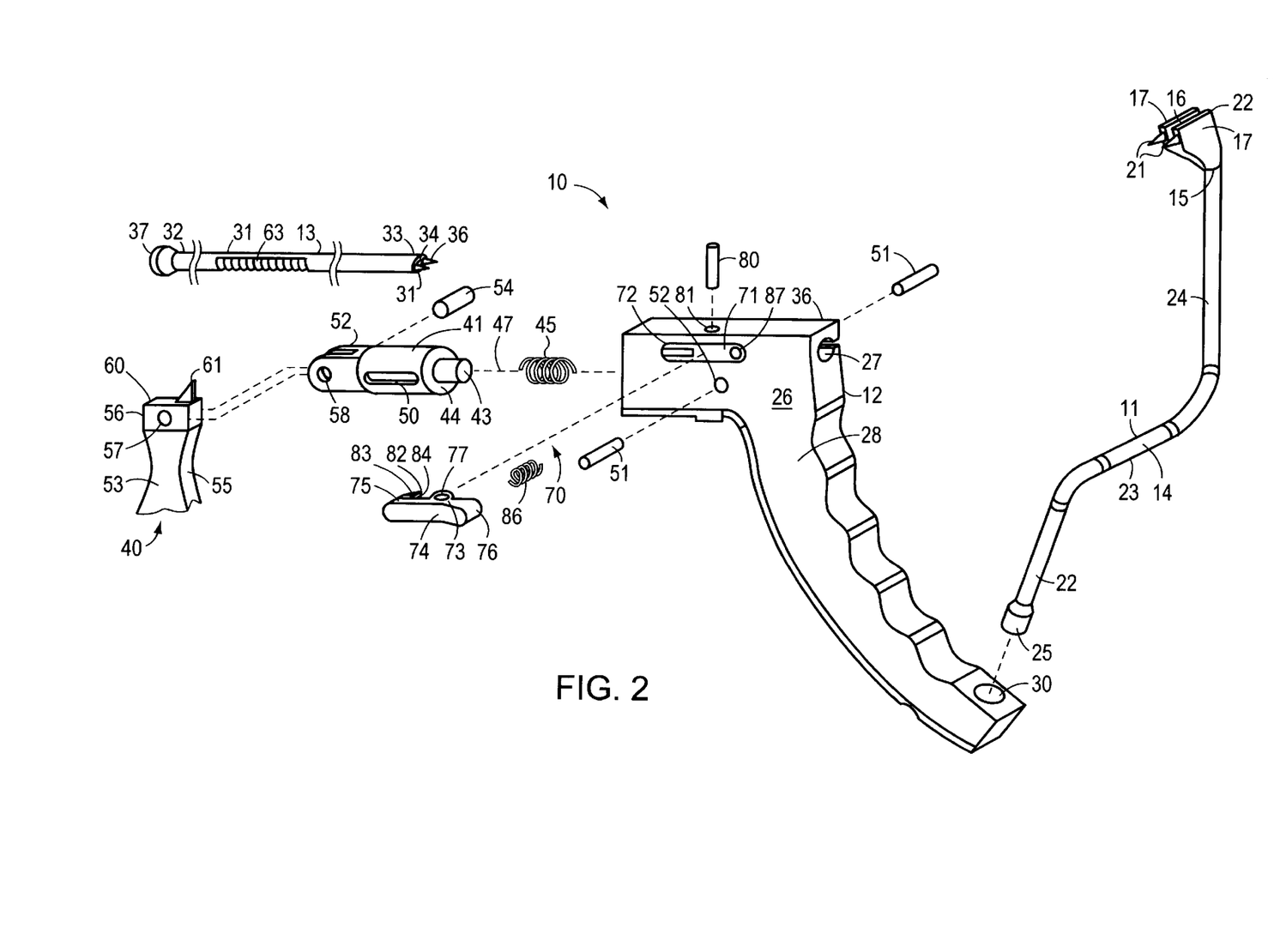
FIG. 2 is an exploded view showing various components of the drill guide in FIG. 1 in perspective.
Figure 3:
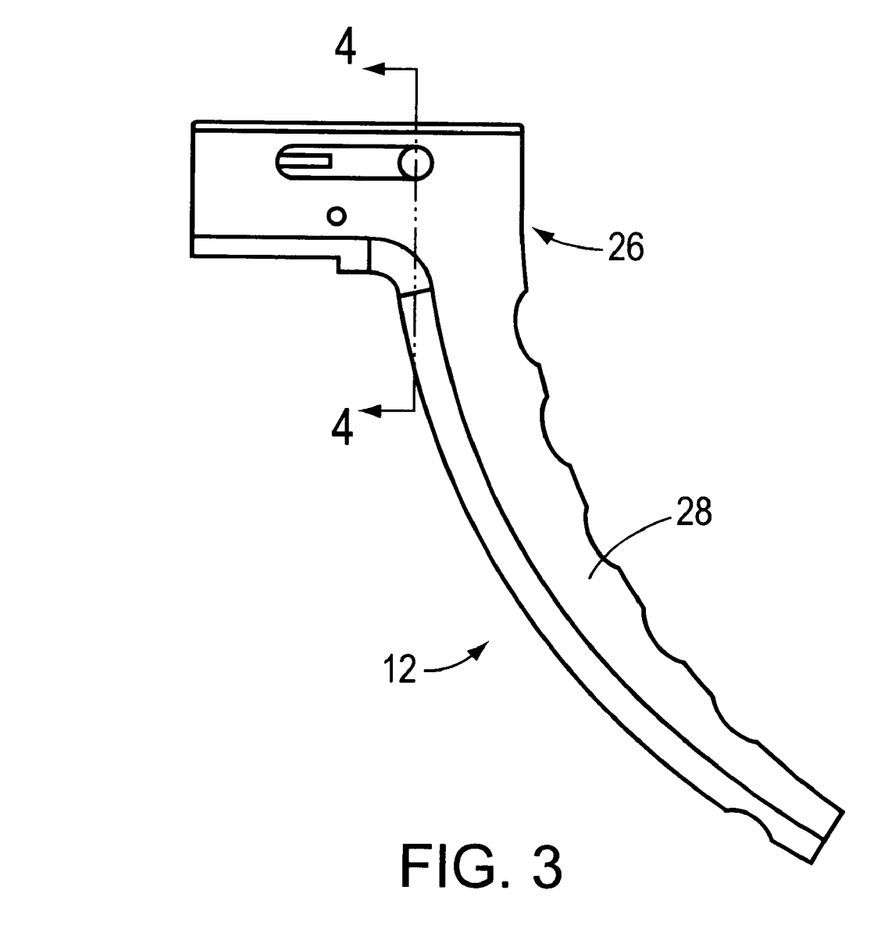
FIG. 3 is a plan view from one side of the handle shown in FIG. 1.

FIGS. 1 and 2 depict a surgical drill guide 10 constructed in accordance with this invention. The three main components of this structural drill guide 10 include a probe 11, a main body 12 and a guide tube 13.

The probe 11 includes an arm 14 that extends from the main body 12 and terminates as a target 15 at the free end of the probe 11. The target 15 includes a yoke 16 with bifurcated yoke arms 17 that extend from the probe. The bifurcation lies on an axis 20 along which the guide tube 13 extends so the guide can pass through the target 15. Each of the yoke arms 17 terminates in a tip 21 that faces the handle 12.

In this specific embodiment the arm 14 comprises three offset sections 22, 23 and 24 that extend from a base component 25. This specific shape is shown by way of example only. It will be apparent that other shapes that position the target 15 on the axis 20 and that allow the target 15 to be positioned in a patient will be acceptable.

Still referring to FIGS. 1 and 2 and the main body 12, a mechanism housing 26 has a generally cylindrical shaped passage 27 formed along the axis 20. A grip portion 28 depends and arcs from the mechanism housing 26 to provide a comfortable finger grip for a surgeon. In this particular embodiment a receptacle 30 located near the free end of the grip portion 28 receives the base 25 to support the probe 11 in the orientation shown in FIG. 1. Thus, the main body 12 carries the probe 11 so the target 15 lies along the axis 20 extending through the passage 27.

The guide tube 13 includes an elongated, cylindrical body 31 extending from a proximal end 32 to a distal end 33. A central passage 34 through the cylindrical body 31 allows a guide wire 35 to pass through the surgical drill guide 10 to contact bone at the distal end 33 of the guide tube 13. To assure appropriate anchoring, the distal end 33 terminates with a pair of pins 36 facing distally toward the target 15. An annular grip 37 at the proximal end of the guide tube 13 facilitates removal of the guide tube 13 from the main body 12 and handling of the guide tube 13 during insertion into the main body 12.

In accordance with this invention, an actuator 40 constitutes a tube advancing mechanism that moves the guide tube 13 in a distal direction by means of a first ratchet and pawl assembly. More specifically, the actuator 40 depends from the main housing 26 and includes a cylinder 41, most clearly seen in FIGS. 2, 7A and 7B, that rides in a cylindrical cavity 42. The cavity 42 is parallel to and below the passage 27. The cylinder 41 includes a reduced radius extension 43 at its distal end that forms a radial shoulder 44.

A spring 45 lies in the cavity 42. The distal end of the spring 45 lies against an end wall 46 and at its proximal end overlies the central extension 43 and abuts the radial shoulder 44. Thus the spring 45 biases the cylinder 41 proximally or to the left in FIG. 2 along an axis 47.

The main body of the cylinder 41 includes an axially extending slot 50. In this particular embodiment another identical slot is positioned on the other side of the cylinder 41. During manufacture the spring 45 and cylinder 41 are loaded in the second passage 42 and moved forward to compress the spring 45. Pins 51 are then pressed into receiving passages 52 to extend into the slots 50. The slots 50 and pins 51 perform two functions. First, they prevent the cylindrical body 41 from rotating about the axis 47 during use. Second, they limit the range of travel of the cylinder 41. This prevents any inadvertent removal of the tube advancing mechanism from the mechanism housing 26. The spring 45 therefore normally will bias the cylinder 41 proximally until the pins 51 reach the proximal ends of the slots 50.

The cylinder also has a distally extending yoke 52 at its proximal end; that is, the end opposite the extension 43. This yoke 52 receives the actuator 40 and a pivot pin 54. More specifically, the actuator 40 includes a base 56 with a cylindrical passage 57 extending transversely to the axis 47. When the actuator 40 is properly positioned between the arms of the yoke 52, the pin 54 passes through apertures 58 in the yoke 52 and the passage 57 in the actuator. Typically the pin 54 will be press fit in the yoke 52, but will allow the actuator 40 to pivot on the pin 54. An upper edge 60 of the actuator 40 includes a thin pawl 61.

Figure 6:
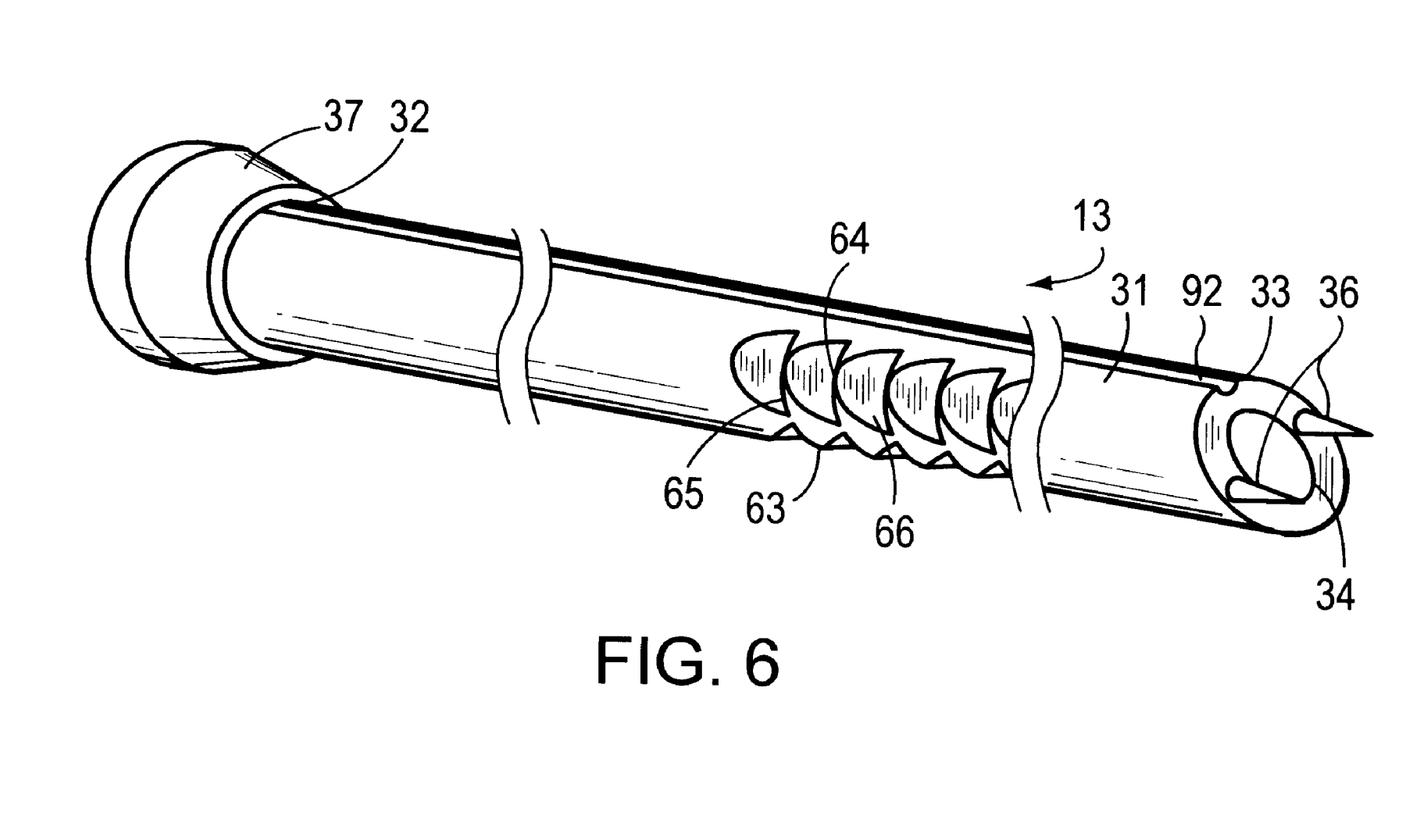
FIG. 6 is an enlarged perspective view of a portion of a guide tube shown in FIG. 1.

Now referring to FIG. 6, the guide tube 13 is formed with first and second sets 63 and 64 of ratchet teeth lying along two surfaces of the guide tube 13. One set 63 of ratchet teeth lies in a plane that faces downward toward the pawl 61 when the guide tube 13 is inserted in the passage 27 through the mechanism housing 26. The second set 64 of ratchet teeth lies in a plane that is at right angles to the set 63. In the orientation shown in FIG. 1, the set 64 is vertical and on the right side of the guide tube 13 when viewed from the proximal end (i.e., from the left in FIG. 1). Each of the sets of ratchet teeth have the same basic form. Each has a vertical surface 65 and a ramped surface 66 extending from the bottom of one vertical surface to the top of the next proximal vertical surface. Thus the vertical surfaces can be considered to be facing proximally within the mechanism housing 26.

Figure 7A:
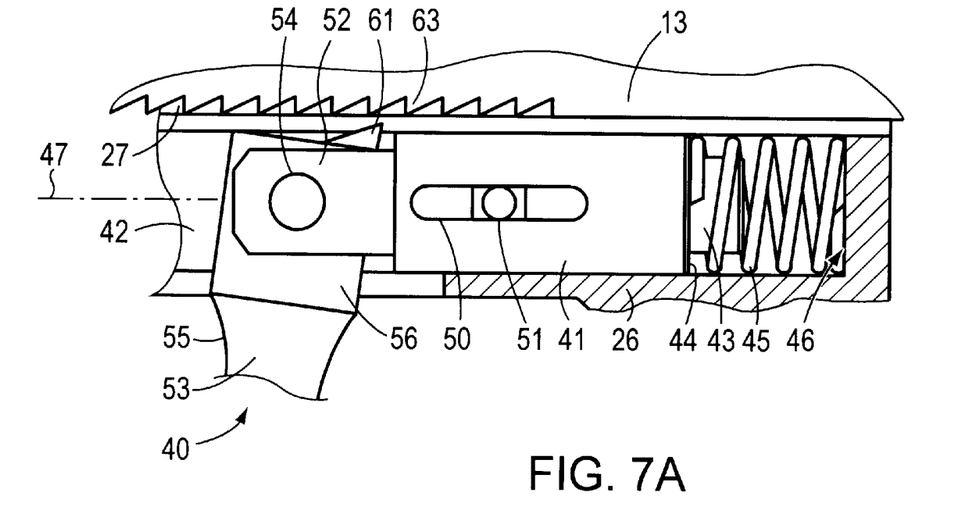
FIGS. 7A and 7B present details of the operation of a tube advancing mechanism shown in FIG. 1.
Figure 7B:
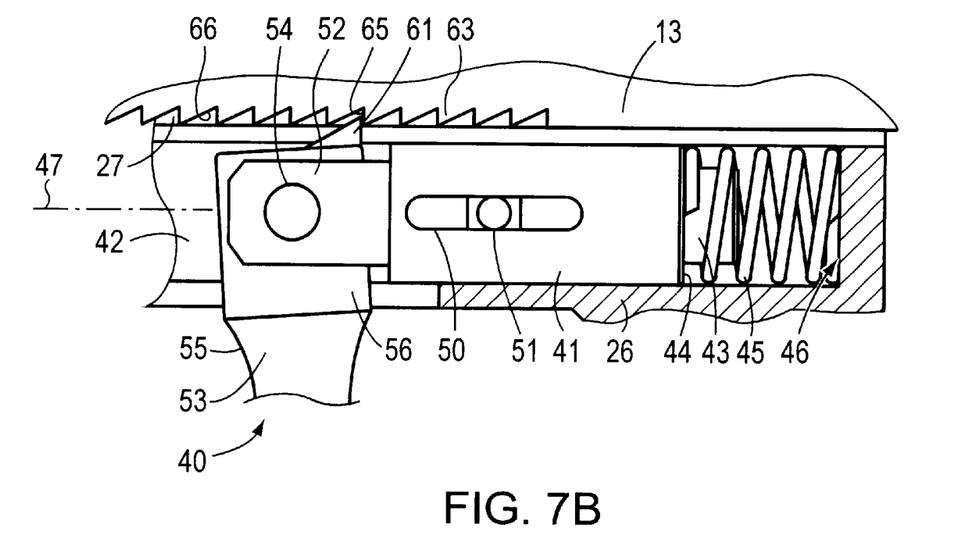

FIG. 7A depicts the actuator 40 in a relaxed position with the spring 45 biasing the cylinder, proximally. When the surgeon squeezes the actuator handle 55, it initially pivots about the pin 54 causing the pawl 61 to elevate against one of the bottom ratchet teeth 63 as shown in FIG. 7B. The point of contact between the pawl 61 and the ratchet teeth 53 can be anywhere along a sloped surface 66. Once the pawl 61 contacts a tooth, continued squeezing causes the cylinder 41 to advance so that the pawl 61 comes into full contact with the distally adjacent vertical surface 65 of the tooth in the ratchet set 63. Consequently as the cylinder 41 travels distally, the pawl 61 drives the guide tube 13 distally. Thus there is a two part action with respect to the actuator 40. The initial action is a rotation of the handle 55 until the pawl 61 contacts a tooth. The second phase occurs when continued pressure on the handle 55 causes the cylinder 41 and handle 55 to displace laterally along the axis 47 and advance the guide tube 13.

When the cylinder 41 reaches its distal most position, a tube locking mechanism comprising a second ratchet and pawl mechanism 70 prevents proximal motion of the guide tube 13, especially while the actuator 40 returns to its first position under the influence of the spring 45. As shown in FIG. 1, mechanism 70 is located in an elongated cavity 71 formed in the side of the mechanism housing 26 centered on the guide axis 20. A passage 72 at the proximal end of the elongated cavity 71 provides access to the side ratchet teeth 64. The cavity carries a rocker 73 that has a body portion 74 extending between a proximal end 75 and a distal end 76. A central transverse passage 77 formed in a boss on the body or centrally located and is vertical when the rocker 73 is located in the elongated cavity 71. A pin 80 is press fit in a passage 81 that extends from the top of the mechanism housing 26 through the elongated cavity 71 and another aligned passage extending below the elongated cavity 71. This pin also passes through the central transverse passage and becomes a pivot for the rocker arm 73. Consequently the rocker arm can move about a vertical axis.

Figure 8A:
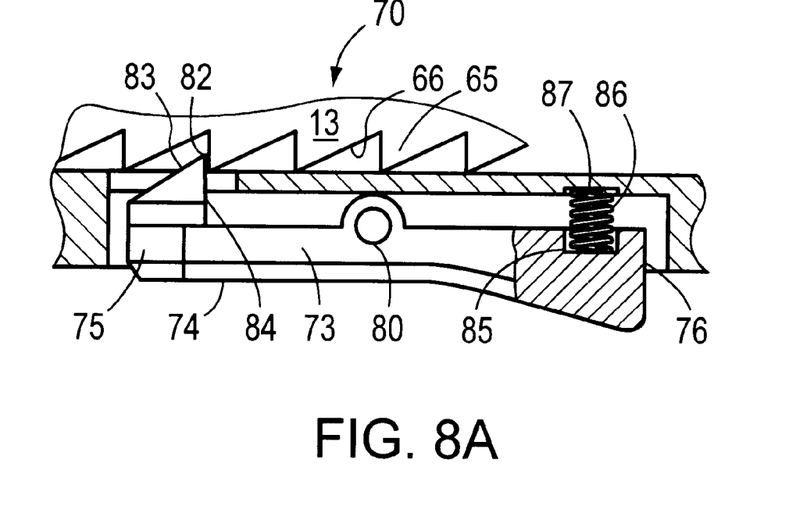
FIGS. 8A and 8B present details of the interaction between a tube locking mechanism shown in FIG. 1.

Referring to FIG. 8A, at the proximal end 75 the rocker 73 carries a pawl 82 with a sloped surface 83 at its proximal side and a vertical surface 84 at the distal side. The pawl 82 extends through the passage to engage a tooth in the side ratchet set 64. At the distal end 76 the rocker 73 includes a receptacle 85 for seating one end of a spring 86 that is captured in a well 87 in the base of the elongated cavity 71. The spring biases the distal end 76 away from the side ratchet teeth 65 thereby forcing the pawl 82 into contact with those teeth. More specifically in this orientation the vertical surface 84 of the pawl engages a vertical tooth surface 65 in the side ratchet teeth 64. This interference between the pawl 82 and the tooth blocks any proximal motion of the guide tube 13.

Figure 8B:
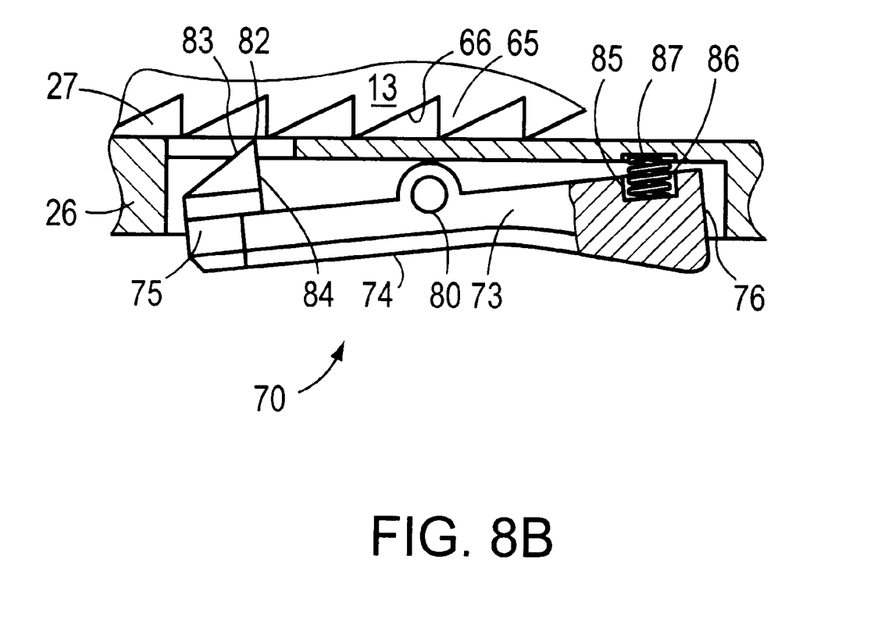

As the guide tube 13 moves distally, either under the control of the actuator 40 or by the direct application of force to the grip portion 28, the pawl 82 rides over the ramped surfaces 66 of the teeth 65. Thus as a surgeon advances the sleeve distally, the pawl 82 allows the guide tube 13 to advance. However, whenever the actuator 40 disengages from the bottom ratchet teeth 63, the pawl 82 then blocks any proximal motion of the guide tube 13. If the surgeon depresses the distal end 76, the rocker 73 pivots about the pin 80 and moves the pawl 82 into a non-interfering position whereupon the guide tube 13 can move freely in either a distal or proximal direction assuming that the actuator 40 is in its normal position.

Figure 4:
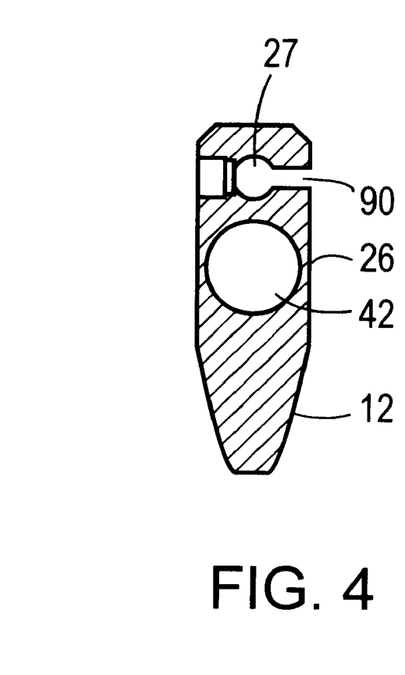
FIG. 4 is a plan view toward the proximal end of the handle shown in FIG. 3.
Figure 5:
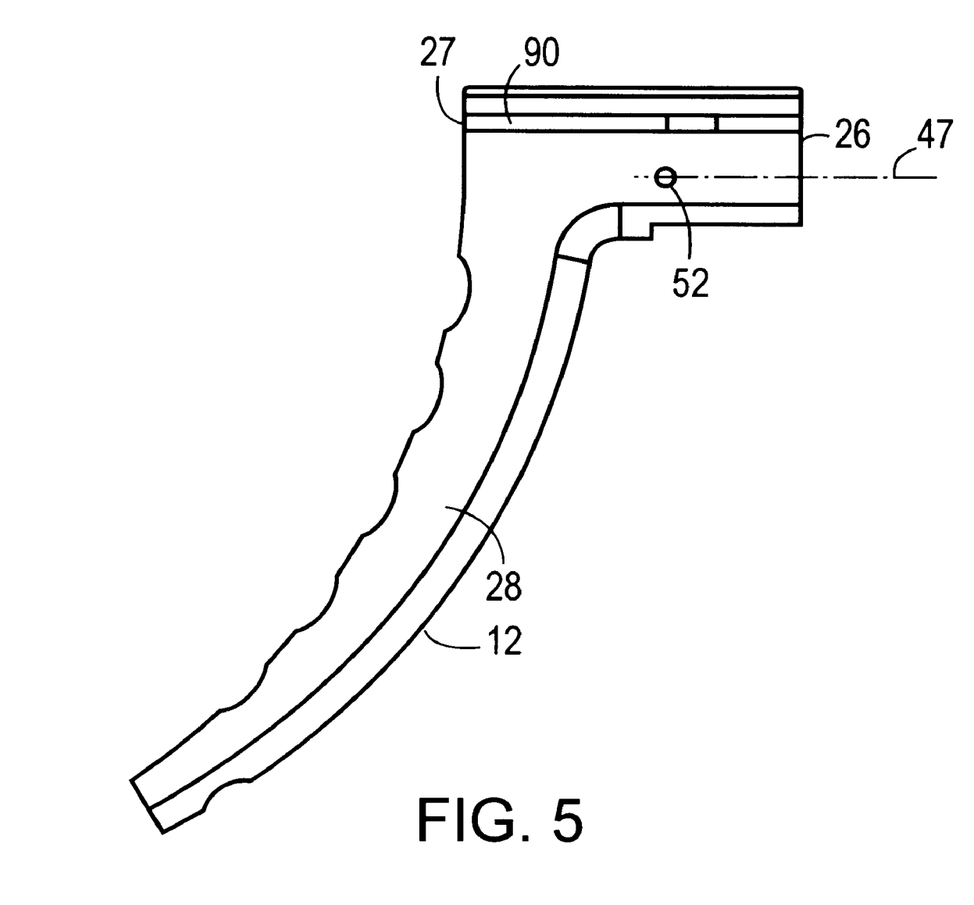
FIG. 5 is a plan view from the other side of the handle shown in FIG. 3.

Referring to FIGS. 4 and 5, the mechanism housing 26 includes the passage for the guide tube 27. As shown most particularly in FIG. 4, the central passage is not closed. A side slot 90 extends through the housing 26 to the guide tube passage 27. As described later, this slot 90 facilitates the removal of the surgical drill guide from a patient after it is used.

Figure 9:
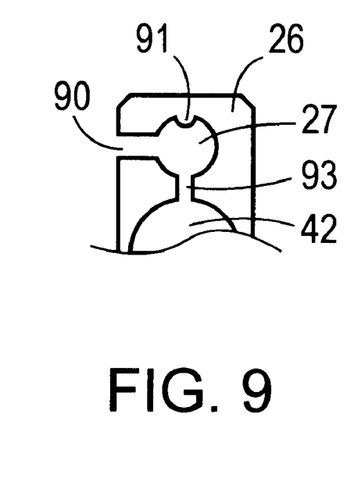
FIG. 9 presents a detail of the interface between portions of the drill guide shown in FIG. 1.

FIGS. 6 and 9 depict another detail of a preferred embodiment of this invention. FIG. 9 is a view taken from the proximal end of the mechanism housing 26. It depicts the guide tube passage 27, the slot 90 and a portion of the passage 42. The mechanism housing 26 additionally includes an integrally formed, axially extending convex radius or key 91. The key 91 can extend along the entire length of the housing 26 or only over a portion of the length. As shown in FIG. 6, the cylindrical body 31 associated with the guide tube 13 includes an axially extending concave radius key way 92. The combination of the key 91 and key way 92 assure that the guide tube 13 is oriented correctly when it is inserted into the guide tube passage 27. They also assure that the guide tube 13 does not rotate in the guide tube passage 27 during use.

FIG. 9 also depicts a passage 93 extending between the guide tube passage 27 and the passage 42 for the cylinder 41. The passage 93 aligns with the pawl 61. Thus, in this embodiment, the pawl 61 extends through the passage 93 to engage the bottom ratchet teeth 63 shown in FIGS. 7A and 7B.

In use, a surgeon positions the surgical drill guide 10 with the target behind a bone. The surgeon inserts the guide tube 13 into the passage 27 and initially advances it merely by applying a force directly to the guide tube 13. When the guide tube 13 is in an approximate position, the surgeon operates the actuator 40 to advance the sleeve distally toward the target to a final position. During this operation, as the pawl 61 advances the guide tube 13 incrementally, the pawl 82 engages a tooth in the side ratchet teeth 64 to prevent any unwanted displacement of the guide tube 13 proximally. Once positioned, the surgeon passes the guide wire through the central passage 34 and anchors its distal end in the bone. Next the surgeon actuates the rocker 73 to release the guide tube 13 and withdraws the guide tube 13 from the surgical drill guide 10 over the proximal end of the guide wire. Then the surgeon manipulates the surgical drill guide 10 to allow the guide wire to pass through the slot 90 and removes the surgical drill guide 10 from the patient.

As will now be apparent, the specifically disclosed embodiment of the surgical drill guide 10 allows a surgeon to position the guide tube 13 in a positive manner. The actuator 40 allows the surgeon to drive the guide tube 13 distally and provides mechanical advantage to assure that the tips 36 on the guide tube 13 firmly engage and anchor the surgical drill guide 10 to the bone. The combination of guide tube advancing mechanism and the tube locking mechanism, each with a ratchet and pawl mechanism, allows the surgeon to perform this portion of the operation with one hand. As positive interference between two elements prevents any unwanted motion, the locking operation is more reliable than those mechanisms that rely entirely upon sliding friction. Use of separate controls in the form of the actuator 40 and the second ratchet pawl mechanism 70 provides a surgical drill guide 10 that is easier to use because the controls are independent of each other. Finally, as will be particularly evident from FIG. 2, the design of the surgical drill guide 10 facilitates its manufacture and minimizes assembly operations.

The foregoing description discusses several specific modifications to a surgical drill guide constructed in accordance with this invention. It will also be apparent that a number of other modifications can be made to this specifically disclosed drill guide 10. The actuators can be located differently. Certain features might be omitted. Different ratchet and pawl mechanisms mights be substituted. Other mechanisms that would still provide positive interference between elements might also be substituted for the ratchet and pawl mechanisms that are disclosed. The drill guides is disclosed with two sets of teeth. These sets could be combined as a single set extending for greater than one-quarter of the guide tube circumference. Therefore, it is the intent of the appended claims to cover all such variations and modifications as come within the true spirit and scope of this invention.

What is claimed as new and desired to be secured by Letters Patent of the United States is:

1. A surgical drill guide comprising:
    A) a body having a base portion with a passage extending therethrough along a body axis, a grip extending from said base portion and a probe extending to a free end spaced distally of said base portion and positioned on the body axis,
    B) a guide tube adapted for being moved through said body passage along the body axis with first and second sets of ratchet teeth formed on angularly displaced faces of said guide tube,
    C) a guide tube advance mechanism with a handle pivoted from said body and a portion for engaging the first set of ratchet teeth thereby to advance said guide tube along the body axis toward the free end of said probe, and
    D) a guide tube locking mechanism with a lever pivoted in said body and biased to a first position wherein said lever engages the second set of ratchet teeth for preventing any motion of said guide tube away from said free end of said probe, said lever disengaging from said second set of ratchet teeth in a second position thereby to enable the movement of said guide tube away from the free end of said probe.

2. A surgical drill guide as recited in claim 1 wherein said first and second sets of ratchets are angularly displaced by 90°.

3. A surgical drill guide as recited in claim 2 additionally including an axially extending closed end cavity extending distally from the proximal end of said body, said guide tube advance mechanism additionally comprising:
    i) a cylinder mounted for axial displacement in said cavity,
    ii) a cylinder spring intermediate the distal end of said cylinder and the closed cavity end,
    iii) a yoke at the proximal end of said cylinder, and
    iv) a pivot mounted to said yoke for carrying said handle.

4. A surgical drill guide as recited in claim 3 wherein said handle includes:
    i) a pawl for engaging said first set of ratchet teeth and extending from a first side of said pivot, and
    ii) a grip portion extending from a second side of said pivot.

5. A surgical drill guide as recited in claim 4 wherein said cylinder includes at least one axially-extending, closed end slot and said base carries a fixed pin for riding in said slot thereby to limit the motion of said cylinder.

6. A surgical drill guide as recited in claim 5 wherein said proximal end of said cylinder forms a shoulder for receiving the proximal end of said cylinder spring.

7. A surgical drill guide as recited in claim 6 wherein said lever in said guide tube locking mechanism has proximal and distal ends and said body includes an axially extending closed end cavity having an opening at its proximal end into said body passage, said guide tube locking mechanism additionally comprising:
    i) a pivot pin mounted in said body through said cavity and a central pivot passage at the center of said lever,
    ii) a lever spring mounted between the distal ends of said lever and said body at said cavity, and
    iii) a pawl extending from the proximal end of said lever, said pawl being positioned in alignment with said proximal cavity opening thereby to be positioned to engage said second set of ratchet teeth.

8. A surgical drill guide as recited in claim 1 wherein said lever in said guide tube locking mechanism has proximal and distal ends and said body includes an axially extending closed end cavity having a proximal opening to said body passage and wherein said guide tube locking mechanism additionally comprises a pivot pin mounted in said body for retaining said lever in said cavity.

9. A surgical drill guide as recited in claim 8 wherein spring retention structures are located at the distal ends of said cavity and said lever, said guide tube locking mechanism additionally including a lever spring intermediate said spring retention structures.

10. A surgical drill guide as recited in claim 9 wherein a pawl extends from the proximal end of said lever in alignment with the opening to said body passage, said lever spring normally forcing said pawl into engagement with a tooth in said second set of ratchet teeth, said distal end of said lever, when depressed, displacing said pawl from said second set of ratchet teeth.

11. A surgical drill guide as recited in claim 1 additionally comprising an alignment mechanism including an axially extending channel on said guide tube and a locator for riding in said channel thereby to align said guide tube angularly within said body passage.

12. A surgical drill guide comprising:
A) a guide tube having a central axially extending passage therethrough,
B) a body having a base portion with a passage extending therethrough along an axis for receiving said guide tube, a grip extending obliquely from said base portion and a probe extending obliquely to a free end positioned on the axis spaced distally of said base portion,
C) a guide tube advance mechanism including a first set of ratchet teeth formed on the exterior of and along a portion of the length of said guide tube and a handle pivoted from said body with a first pawl for engaging said first set of ratchet teeth in a first position whereby actuation of said guide tube advance mechanism moves said guide tube distally for an incremental distance, said pawl being spaced from said first set of ratchet teeth in a second position, and
D) a guide tube locking mechanism including a second set of ratchet teeth formed on the exterior of and along a portion of the length of said guide tube and a lever with a second pawl pivoted in said body and biased to a first position whereby said second pawl engages a tooth in said second set of ratchet teeth thereby to prevent any motion of said guide tube away from said arm, said lever disengaging said second pawl from said second set of ratchet teeth in a second position thereby to enable the movement of said guide tube away from the free end of said arm.

13. A surgical drill guide as recited in claim 12 wherein said guide tube advancing mechanism additionally includes a first spring for biasing said first pawl to the second position and said guide tube locking mechanism additionally includes a second spring for biasing said second pawl to the first position.

14. A surgical drill guide as recited in claim 13 wherein said handle in said guide tube advancing mechanism additionally includes an intermediate pivot displaced from said first pawl and a grip that extends from said intermediate pivot and away from said first pawl.

15. A surgical drill guide as recited in claim 14 wherein said body has an axially extending closed end cavity extending distally from the proximal end of said body and said guide tube advance mechanism additionally comprises:
i) a cylinder mounted for axial displacement in said cavity, said first spring being located intermediate the distal end of said cylinder and the closed cavity end,
ii) a yoke at the proximal end of said cylinder, and
iii) a pivot pin mounted to said yoke and through said handle pivot.

16. A surgical drill guide as recited in claim 15 additionally comprising an alignment mechanism including an axially extending channel on said guide tube and a locator for riding in said channel thereby to align said guide tube angularly within said body passage.

17. A surgical drill guide as recited in claim 14 wherein said guide tube locking mechanism additionally includes:
i) a pivot pin mounted in said body through said cavity, said pivot pin passing through a central pivot passage at the center of said lever,
ii) a lever spring mounted between the distal ends of said lever and said cavity, and
iii) a lever pawl extending from the proximal end of said lever pawl, said pawl being positioned in alignment with said proximal cavity opening thereby to be positioned to engage said second set of ratchet teeth.

18. A surgical drill guide as recited in claim 17 additionally comprising an alignment mechanism including an axially extending channel on said guide tube and a locator for riding in said channel thereby to align said guide tube angularly within said body passage.

19. A surgical drill guide as recited in claim 13 wherein said guide tube locking mechanism additionally includes:
i) a pivot pin mounted in said body through said cavity, said pivot pin passing through a central pivot passage at the center of said lever,
ii) a lever spring mounted between the distal ends of said lever and said cavity, and
iii) a lever pawl extending from the proximal end of said lever, said lever pawl being positioned in alignment with said proximal cavity opening thereby to be positioned to engage said second set of ratchet teeth.

20. A surgical drill guide comprising:
A) a guide tube having a central axially extending passage therethrough;
B) a body having a base portion with an axially extending passage, a grip extending obliquely from said base portion and a probe extending obliquely to a free end positioned on the axis and spaced distally of said base portion;
C) a guide tube advance mechanism including:
i) a first set of ratchet teeth formed on the exterior of and along a portion of the length of said guide tube,
ii) a handle pivoted from said body with a first pawl for engaging said first set of ratchet teeth in a first position whereby actuation of said guide tube advance mechanism moves said guide tube distally for an incremental distance, said pawl being spaced from said first set of ratchet teeth in a second position,
iii) a cylinder mounted for axial displacement in said body,
iv) a spring intermediate the distal end of said cylinder and the closed cavity end,
v) a yoke at the proximal end of said cylinder, and
vi) a pivot mounted to said yoke for carrying said handle; and
D) a guide tube locking mechanism including:
i) a second set of ratchet teeth formed on the exterior of and along a portion of the length of said guide tube,
ii) a lever with a second pawl pivoted in said body and biased to a first position whereby said second pawl engages a tooth in said second set of ratchet teeth thereby to prevent any motion of said guide tube away from said arm, said lever disengaging said second pawl from said second set of ratchet teeth in a second position thereby to enable the movement of said guide tube away from the free end of said arm,
iii) an axially extending cavity formed in said body having an opening at its proximal end into said body passage and said guide tube locking mechanism,
iv) a pivot pin mounted in said body through said cavity, said pivot pin passing through a central pivot passage at the center of said lever, and
v) a lever spring mounted between the distal ends of said lever and said cavity.

* * * * *